(12) United States Patent
Ali et al.

(10) Patent No.: US 11,686,701 B2
(45) Date of Patent: Jun. 27, 2023

(54) NANOPORE DEVICE AND METHODS OF DETECTING AND CLASSIFYING CHARGED PARTICLES USING SAME

(71) Applicant: PALOGEN, INC., Palo Alto, CA (US)

(72) Inventors: Imran Ali, Gyeonggi-do (KR); Kyung Joon Han, Palo Alto, CA (US); Kang-Yoon Lee, Seoul (KR)

(73) Assignee: PALOGEN, INC., Palo Alto, CA (US)

( * ) Notice: Subject to any disclaimer, the term of this patent is extended or adjusted under 35 U.S.C. 154(b) by 369 days.

(21) Appl. No.: 16/930,504

(22) Filed: Jul. 16, 2020

(65) Prior Publication Data

US 2021/0018464 A1    Jan. 21, 2021

Related U.S. Application Data

(60) Provisional application No. 62/874,766, filed on Jul. 16, 2019.

(51) Int. Cl.
*G01N 27/416* (2006.01)
*B01L 3/00* (2006.01)
*C12Q 1/6869* (2018.01)
*G01N 27/447* (2006.01)
*G01N 33/487* (2006.01)

(52) U.S. Cl.
CPC .... *G01N 27/4163* (2013.01); *B01L 3/502761* (2013.01); *C12Q 1/6869* (2013.01); *G01N 27/44791* (2013.01); *G01N 33/48721* (2013.01); *B01L 2200/0647* (2013.01)

(58) Field of Classification Search
None
See application file for complete search history.

(56) References Cited

U.S. PATENT DOCUMENTS

2017/0370903 A1* 12/2017 Mager .............. G01N 27/44791
2019/0101524 A1    4/2019 Han et al.

OTHER PUBLICATIONS

PCT International Search Report and Written Opinion for International Appln. No. PCT/US2020/042273, applicant Palogen, Inc., dated Aug. 10, 2020 (9 pages).
PCT International Preliminary Report on Patentability for International Appln. No. PCT/US2020/042273, applicant Palogen, Inc., dated Jan. 18, 2022.

* cited by examiner

*Primary Examiner* — J. Christopher Ball
(74) *Attorney, Agent, or Firm* — Vista IP Law Group LLP

(57) ABSTRACT

A method of calibrating a nanofluidic device including a plurality of nanopore channels, a plurality of gating nanoelectrodes, and a plurality of sensing nanoelectrodes, includes applying a selecting voltage across a gating nanoelectrode of the plurality of gating nanoelectrodes to select a nanopore channel. The method also includes tuning the nanopore channel by applying a first biasing voltage across a sensing electrode of the plurality of sensing nanoelectrodes, and receiving a plurality of currents over a plurality of frequencies. The method further includes generating a calibration data set from the pluralities of frequencies and currents. Moreover, the method includes comparing the calibration data set with a reference data set. In addition, the method includes when the calibration data set differs from the reference data set by more than a predetermined threshold, repeating the method with a second biasing voltage different from the first biasing voltage.

16 Claims, 11 Drawing Sheets

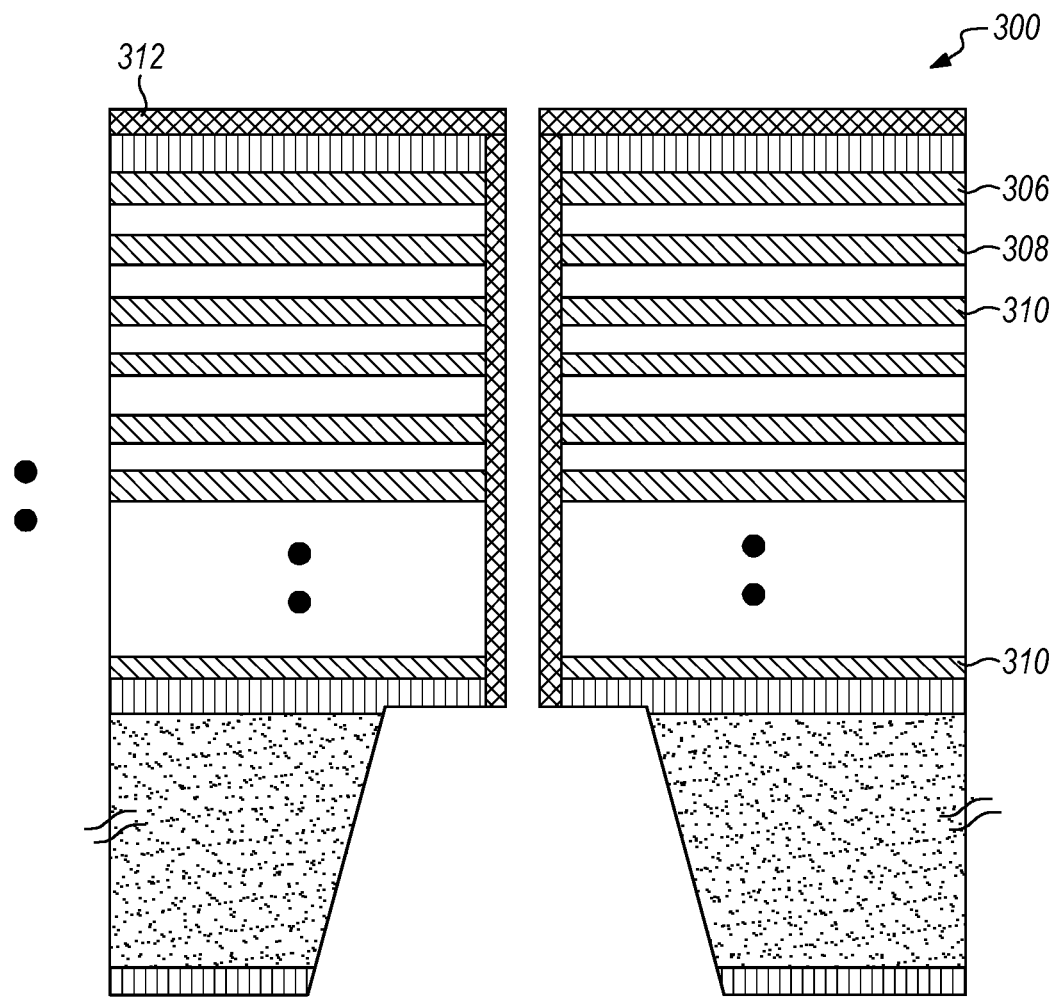
FIG. 3
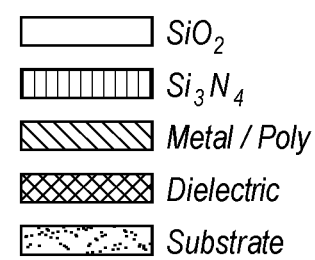

(a) Pre-Calibration (b) Post-Calibration (a) Pre-Calibration Algorithm (b) Post-Calibration Algorithm

NANOPORE DEVICE AND METHODS OF DETECTING AND CLASSIFYING CHARGED PARTICLES USING SAME

CROSS-REFERENCE TO RELATED APPLICATION

This application claims priority to U.S. Provisional Application No. 62/874,766, filed on Jul. 16, 2019 and, entitled "NANOPORE DEVICE AND METHODS OF DETECTING AND CLASSIFYING CHARGED PARTICLES USING SAME," the contents of which are hereby expressly and fully incorporated by reference in their entirety, as though set forth in full. This application includes subject matter similar to the subject matter described in co-owned U.S. Provisional Patent Application Ser. No. 62/566,313, filed on Sep. 29, 2017 and entitled "MANUFACTURE OF THREE DIMENSIONAL NANOPORE DEVICE"; U.S. Provisional Patent Application Ser. No. 62/593,840, filed on Dec. 1, 2017 and entitled "NANOPORE DEVICE AND METHOD OF MANUFACTURING SAME"; U.S. Provisional Patent Application Ser. No. U.S. Provisional Patent Application Ser. No. 62/612,534, filed on Dec. 31, 2017 under and entitled "NANOPORE DEVICE AND METHODS OF ELECTRICAL ARRAY ADDRESSING AND SENSING"; U.S. Provisional Patent Application Ser. No. 62/628,214, filed on Feb. 8, 2018 and entitled "BIOMEMORY FOR NANOPORE DEVICE AND METHODS OF MANUFACTURING SAME"; U.S. Provisional Patent Application Ser. No. 62/711,234, filed on Jul. 27, 2018 and entitled "NANOPORE DEVICE AND METHODS OF DETECTING CHARGED PARTICLES USING SAME"; U.S. Utility patent application Ser. No. 16/147,362, filed on Sep. 26, 2018 and entitled "NANOPORE DEVICE AND METHOD OF MANUFACTURING SAME"; U.S. Utility patent application Ser. No. 16/237,570, filed on Dec. 31, 2018 and entitled "NANOPORE DEVICE AND METHODS OF ELECTRICAL ARRAY ADDRESSING AND SENSING"; U.S. Provisional Patent Application Ser. No. 62/802,459, filed on Feb. 7, 2019 and entitled "BIOMEMORY FOR NANOPORE DEVICE AND METHODS OF MANUFACTURING SAME"; and U.S. Provisional Patent Application Ser. No. 62/826,897, filed on Mar. 29, 2019 and entitled "NANOPORE DEVICE AND METHODS OF BIOSYNTHESIS USING SAME." The contents of the above-mentioned applications are fully incorporated herein by reference as though set forth in full.

FIELD OF THE INVENTION

The present invention relates generally to systems and devices for classifying biopolymer molecules, and methods of detecting charged biopolymer molecules using such systems and devices. In particular, the present invention relates to nanopore sensors for detecting charged biopolymer molecules, methods of calibrating same, and methods of classifying biopolymer molecules using same.

BACKGROUND

Many diseases like cancers are curable if detected early before the disease has progressed. However, millions of people die annually from such "curable" diseases. An affordable and rapid point of care detection device for the accurate and early diagnosis of the cancers in low-level stages would allow early treatment, thereby reducing morbidity and mortality.

As a result of the human genome project, many disease-related mutations (e.g., cancer-related) in the human genome can now be detected by probing for gene polymorphisms. Similarly, many disease causing organisms (e.g., viruses) can also be detected by probing for their specific gene sequences. Detection of target genes/sequences of interest in around 10 minutes can facilitate point of care detection for diagnosis disease, determining disease prognosis, and/or monitoring of disease.

Mutation is common in nucleic acid (e.g., DNA, RNA, etc.) replication. In fact, mutation is a driving force behind natural selection and evolution. Mutation results in genetic/gene polymorphisms in populations, which can be linked to blood types, genetic diseases, etc. Detection of gene polymorphisms is one of the most powerful methods to identify genetic variations at the molecular level. Many signatures of genetic diseases can be detected by information collected through detecting gene polymorphisms such as single nucleotide polymorphisms ("SNPs"), small-scale insertions/deletions ("Indels"), transposable elements, and microsatellites, etc. Many gene polymorphism detection techniques require nuclei acid amplification (e.g., using PCR) and/or tagging/labeling of gene probes (e.g., with enzymes/radio-isotopes). These molecular biology techniques are expensive and time-consuming.

Gene polymorphisms can also be "detected" using whole genome sequencing, which is another expensive and time-consuming technique. Current technologies to sequence nucleic acids at the single molecule level include a nanopore sequencing technology that has advantages over previous sequencing techniques because nanopore sequencing technology has the characteristics of a tag-free, label-free, and amplification-free technique that also has improved read lengths, and improved system throughput. Accordingly, nanopore sequencing technology has been incorporated into high-quality gene sequencing applications.

Early experimental systems for nanopore based DNA sequencing detected electrical behavior of ssDNA passing through an α-hemolysin (αHL) protein nanopore. Since then, nanopore based nucleic acid sequencing technology has been improved. For instance, solid-state nanopore based nucleic acid sequencing replaces biological/protein based nanopores with solid-state (e.g., semiconductor, metallic gates) nanopores, as described below.

A nanopore is a small hole (e.g., with a diameter of about 1 nm to about 100 nm) that can detect the flow of charged particles (e.g., ions, molecules, etc.) through the hole by the change in the ionic current and/or tunneling current. Because each nucleotide of a nucleic acid (e.g., adenine, cytosine, guanine, thymine in DNA, uracil in RNA) affects the electric current density across the nanopore in a specific manner as it physically passes through the nanopore, measuring changes in the current flowing through a nanopore during translocation results in data that can be used to directly sequence a nucleic acid molecule passing through the nanopore. As such, Nanopore technology is based on electrical sensing, which is capable of detecting nucleic acid molecules in concentrations and volumes much smaller than that required for other conventional sequencing methods. Advantages of nanopore based nucleic acid sequencing include long read length, plug and play capability, and scalability. With advancements in semiconductor manufacturing technologies, solid-state nanopores have become an inexpensive and superior alternative to biological nanopores partly due to the superior mechanical, chemical and thermal characteristics, and compatibility with semiconductor technology allowing the integration with other sensing circuitry and nanodevices.

FIG. 1 schematically depicts a state-of-art solid-state based 2-dimensional ("2D") nanopore sequencing device 100. While, the device 100 is referred to as "two dimensional," the device 100 has some thickness along the Z axis. In order to address the some of these drawbacks (sensitivity and some of the manufacturing cost) of current state-of-art nanopore technologies, multi-channel nanopore arrays which allows parallel processing of biomolecule sequencing may be used to achieve tag-free, label-free, amplification-free, and rapid sequencing. Examples of such multi-channel nanopore arrays are described in U.S. Provisional Patent Application Ser. Nos. 62/566,313 and 62/593,840, the contents of which have been previously incorporated by reference.

While nanopore devices have been used to sequence nucleic acid polymers with increasing efficiency and effectiveness, whole genome sequencing is overly complicated for detection of particular gene polymorphisms. For instance, target gene of interest detection involves much smaller and manageable data compare with routine amplification based methods such as whole genome sequencing that involve large data sets. 3D nanopore array systems, such as those described in U.S. Provisional Patent Application Ser. No. 62/711,234, the contents of which have been previously incorporated by reference, provide more efficient, tag-free, label-free, amplification-free, and rapid sequencing of biopolymers. However, such complex 3D nanopore arrays require correspondingly intricate calibration. There is a need for efficient and rapid methods of calibrating 3D nanopore array systems. Rapid sequencing of biopolymers generates large amounts of biopolymer related raw data. However, detection of biopolymer (e.g., gene) polymorphisms indicative of various conditions and diseases requires classification of that biopolymer related raw data. In particular, there is a need for accurate, efficient, and rapid classification of biopolymer related raw data in the detection of polymorphisms and the corresponding conditions and diseases.

SUMMARY

Embodiments described herein are directed to nanopore based gene polymorphism detection systems and methods of calibrating same and detecting gene polymorphisms using same. In particular, the embodiments are directed to various types (2D or 3D) of nanopore based gene polymorphism detection systems, methods of calibrating and using nanopore array devices, and methods of gene polymorphism detection using same.

In one embodiment, a method of calibrating a nanofluidic device including a plurality of nanopore channels, a plurality of gating nanoelectrodes, and a plurality of sensing nanoelectrodes, includes a) applying a selecting voltage across a gating nanoelectrode of the plurality of gating nanoelectrodes to select a nanopore channel corresponding to the gating nanoelectrode. The method also includes b) tuning the nanopore channel by applying a first biasing voltage across a sensing electrode of the plurality of sensing nanoelectrodes corresponding to the nanopore channel, and receiving a plurality of currents over a plurality of frequencies from the sensing electrode in response to the applied first biasing voltage. The method further includes c) generating a calibration data set from the pluralities of frequencies and currents. Moreover, the method includes d) comparing the calibration data set with a reference data set. In addition, the method includes e) when the calibration data set differs from the reference data set by more than a predetermined threshold, repeating steps b) to d) with a second biasing voltage different from the first biasing voltage.

In one or more embodiments, the method also includes f) when the calibration data set is within the predetermined threshold of the reference data set, storing respective values of the selecting voltage and a final biasing voltage, wherein when the final biasing voltage is applied to the sensing electrode, the calibration data set is within the predetermined threshold of the reference data set. The method may also include, when the calibration data set is within the predetermined threshold of the reference data set, g) applying the selecting voltage and the final biasing voltage across the gating and sensing nanoelectrodes, respectively, h) receiving a second plurality of currents over a second plurality of frequencies from the sensing electrode in response to the applied final biasing voltage, i) generating a detected data set from the second pluralities of frequencies and currents, and j) applying a temperature compensation to the detected data set to generate a final detected data set.

In one or more embodiments, the method also includes, when the calibration data set is within the predetermined threshold of the reference data set, k) storing the respective values of the selecting voltage and the final biasing voltage, and the final detected data set. The method may include repeating steps a) to k) with each of the plurality of nanopore channels. Steps a) to k) may be performed with digital current data. The method may include analyzing the respective values of the selecting voltage and the final biasing voltage, and the final detected data set to identify an oligonucleotide. The oligonucleotide may be associated with a genetic condition.

In one or more embodiments, the plurality of currents are received from an analog to digital converter. The analog to digital converter may generate digital current data from analog current data. The digital current data may correspond to a plurality of nucleotides. The method may include repeating steps a) to e) with each of the plurality of nanopore channels.

In one or more embodiments, selecting voltage is applied across VG1 and VG2. The first biasing voltage may be applied across VG3 and VG4. The reference data set may correspond to a Gaussian curve. The second biasing voltage may be determined by analyzing the calibration data set and the first biasing voltage. The method may include amplifying the plurality of currents.

The aforementioned and other embodiments of the invention are described in the Detailed Description which follows.

BRIEF DESCRIPTION OF THE DRAWINGS

The drawings described below are for illustration purposes only. The drawings are not intended to limit the scope of the present disclosure. The drawings illustrate the design and utility of various embodiments of the present disclosure. It should be noted that the figures are not drawn to scale and that elements of similar structures or functions are represented by like reference numerals throughout the figures. In order to better appreciate how to obtain the recited and other advantages and objects of various embodiments of the disclosure, a more detailed description of the present disclosure will be rendered by reference to specific embodiments thereof, which are illustrated in the accompanying drawings. Understanding that these drawings depict only typical embodiments of the disclosure and are not therefore to be considered limiting of its scope, the disclosure will be described and explained with additional specificity and detail through the use of the accompanying drawings.

FIG. 1 schematically illustrates a prior art solid-state 2D nanopore device;

FIGS. 2 to 4 schematically illustrate 3D nanopore devices according to various embodiments.

Figure 1:
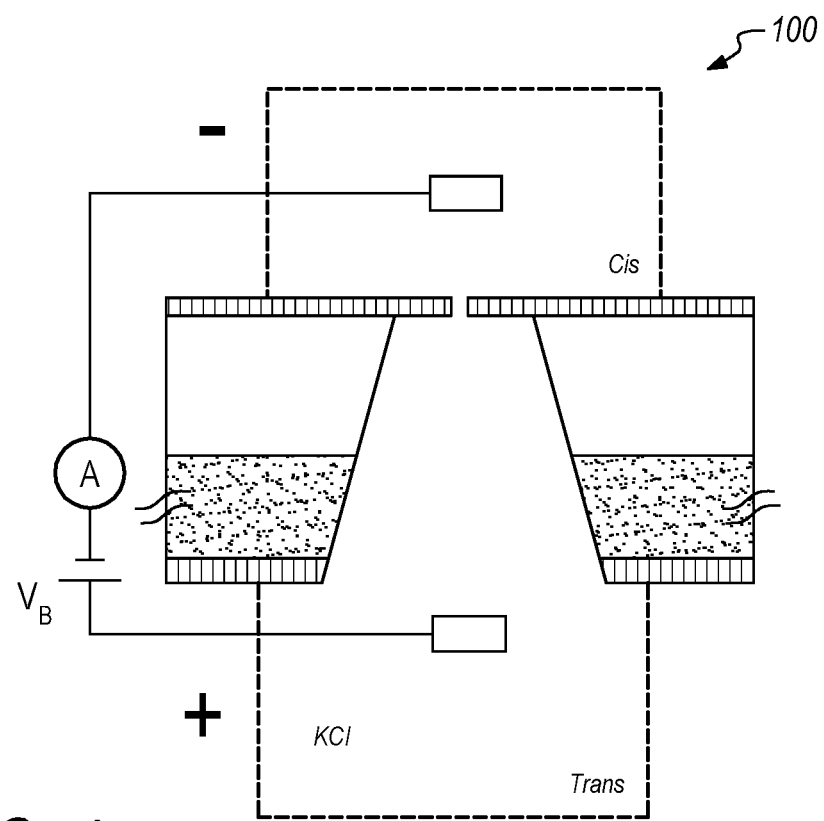

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

In order to address the above-described 3D nanopore array calibration and polymorphism classification limitations, methods are described herein for calibrating nanopore gene polymorphism detection devices and methods are also described herein for classifying biopolymer sequences to achieve tag-free, label-free, amplification-free, and rapid detection of gene polymorphisms (e.g., in under 10 minutes). Calibration and classification systems and methods are described below that facilitate nanopore gene polymorphism detection devices and methods to efficiently and effectively detect polymorphisms. Such detection devices and methods can be used in various biomolecular arrays, including microarrays, CMOS arrays, and nanopore arrays (e.g., solid-state, biological, and hybrid nanopore arrays). Such detection devices and methods can also be used with various multi-channel nanopore arrays, including the 3D multi-channel nanopore arrays described above and planar multi-channel nanopore arrays.

Multi-channel nanopore arrays that allow parallel processing of charged biomolecule detection may be used to achieve tag-free, label-free, amplification-free, and rapid biomolecule detection. Examples of such multi-channel nanopore arrays are described in U.S. Provisional Patent Application Ser. Nos. 62/566,313 and 62/593,840, the contents of which have been previously incorporated by reference. Such multi-channel nanopore arrays can be electrically addressed to direct charged particles (e.g., biomolecules) to specific channels in these multi-channel nanopore arrays. Other arrays are coupled to microfluidic channels outside the array. Electrically addressing and sensing individual nanopore channels within multi-channel nanopore arrays, as described in U.S. Provisional Patent Application Ser. No. 62/612,534, the contents of which have been previously incorporated by reference, can facilitate more efficient and effective use of multi-channel nanopore arrays to achieve low cost, high throughput, tag-free, label-free, amplification-free detection of charged particles (e.g., biomolecules).

Exemplary Nanopore Devices

Figure 2:
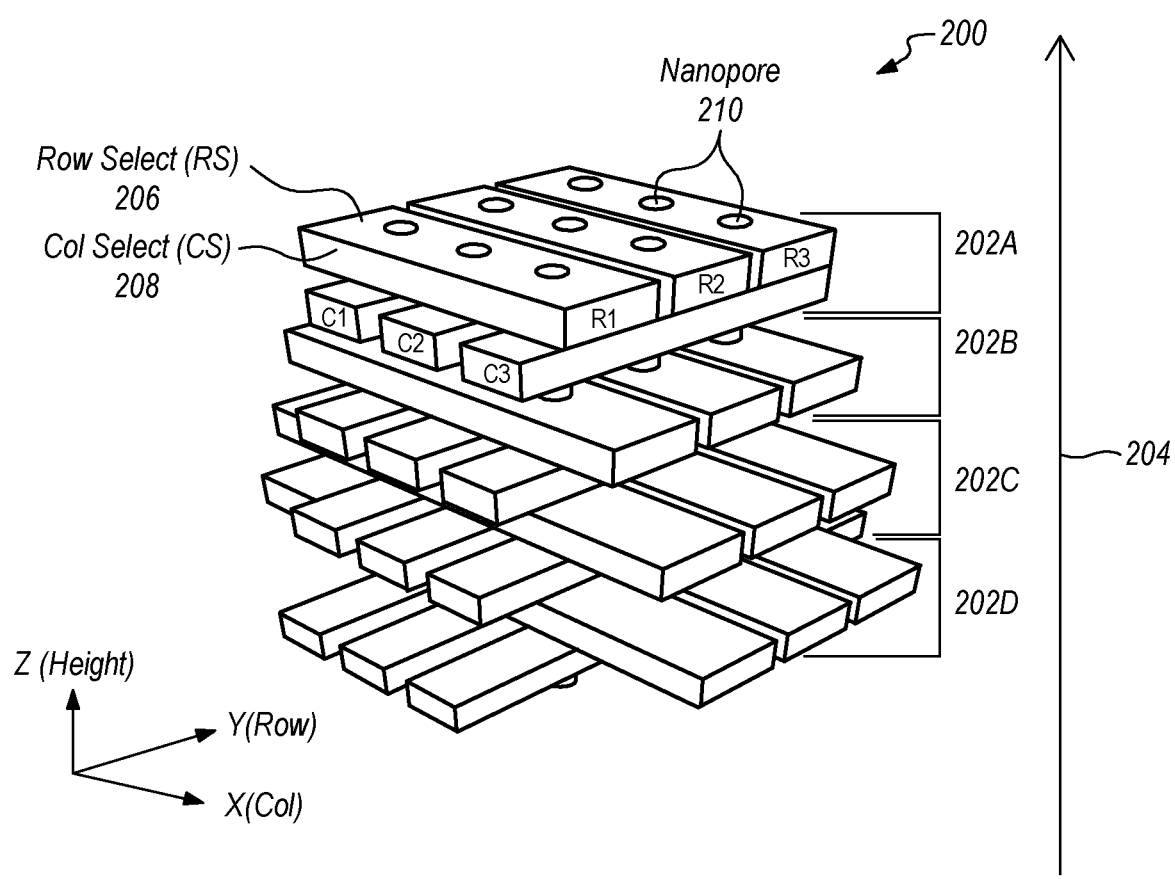

FIG. 2 schematically depicts a nanopore device 200 with a three dimensional ("3D") array architecture according to one embodiment. The device 200 includes a plurality of 2D arrays or layers 202A-202E stacked along a Z axis 204. While the 2D arrays 202A-202E are referred to as "two dimensional," each of the 2D arrays 202A-202E has some thickness along the Z axis.

The top 2D array 202A includes first and second selecting (inhibitory nanoelectrode) layers 206, 208 configured to direct movement of charged particles (e.g., biopolymers) through the nanopores 210 (pillars, nanochannels) formed in the first and second selecting layers 206, 208. The first selecting layer 206 is configured to select from a plurality of rows (R1-R3) in the 2D array 202A. The second selecting layer 208 is configured to select from a plurality of columns (C1-C3) in the 2D array 202A. In one embodiment, the first and second selecting layers 206, 208 select from the rows and columns, respectively, by modifying a charge adjacent the selected row and column and/or adjacent to the non-selected rows and columns. The other 2D arrays 202B-202E include rate control/current sensing nanoelectrodes. Rate control/sensing nanoelectrodes may be made of highly conductive metals and polysilicon, such as Au—Cr, TiN, TaN, Ta, Pt, Cr, Graphene, Al—Cu, etc. The rate control/sensing nanoelectrodes may have a thickness of about 0.3 to about 1000 nm. Rate control/sensing nanoelectrodes may also be made in the biological layer in hybrid nanopores. Each sensing nanoelectrode may be operatively coupled/address to a nanopore 210 pillar, such that each nanopore 210 pillar may be operatively coupled to a particular memory cell. Electrical addressing in nanopore devices is described in U.S. Provisional Patent Application Ser. No. 62/612,534, the contents of which have been previously incorporated by reference.

Hybrid nanopores include a stable biological/biochemical component with solid-state components to form a semi-synthetic membrane porin to enhance stability of the nanopore. For instance, the biological component may be an αHL molecule. The αHL molecule may be inserted into a SiN based 3D nanopore. The αHL molecule may be induced to take on a structure to ensure alignment of the αHL molecule with the SiN based 3D nanopore by apply a bias to a nanoelectrode (e.g., in the top 2D array 202A).

The nanopore device 200 has a 3D vertical pillar stack array structure that provides a much larger surface area for charge detection than that of a conventional nanopore device having a planar structure. As a charged particle (e.g., biopolymer) passes through each 2D array 202A-202E in the device, its charge can be detected with a detector (e.g., nanoelectrode) in some of the 2D arrays 202B-202E. Therefore, the 3D array structure of the device 200 facilitates higher sensitivity, which can compensate for a low signal detector/nanoelectrode. The integration of memory cells into the 3D array structure minimizes any memory related performance limitations (e.g., with external memory device). Further, the highly integrated small form factor 3D structure provides a high density nanopore array while minimizing manufacturing cost.

In use, the nanopore device 200 is disposed between and separating top and bottom chambers (not shown) such that the top and bottom chambers are fluidly coupled by the nanopore pillars 210. The top and bottom chambers include a nanoelectrode (e.g., Ag/AgCl$_2$, etc.) and electrolyte solutions (KCl) containing the charged particles (e.g., DNA) to be detected. Different nanoelectrodes and electrolyte solutions can be used for the detection of different charged particles.

Electrophoretic charged particle translocation can be driven by applying a bias to nanoelectrodes disposed in a top chamber (not shown) adjacent the top 2D array 202A of the nanopore device 200 and a bottom chamber (not shown) adjacent the bottom 2D array 202E of the nanopore device 200. In some embodiments, the nanopore device 200 is disposed in a between top and bottom chambers (not shown) such that the top and bottom chambers are fluidly and electrically coupled by the nanopore pillars 210 in the nanopore device 200. The top and bottom chambers may contain the electrolyte solution.

FIG. 3 schematically depicts a nanopore device 300 according to one embodiment. The nanopore device 300 includes an insulating membrane layer (Si$_3$N$_4$) followed by row and column select (inhibitory nanoelectrodes) 306 and 308, respectively (e.g., metal or doped polysilicon), and a plurality ($1^{st}$ to $N^{th}$) of cell nanoelectrodes 310 (e.g., metal or doped polysilicon). The nanoelectrodes 306, 308, 310 of the nanopore device 300 are covered by an insulator dielectric film 312 (e.g., Al$_2$O$_3$, HfO$_2$, SiO$_2$, ZnO).

Figure 4:
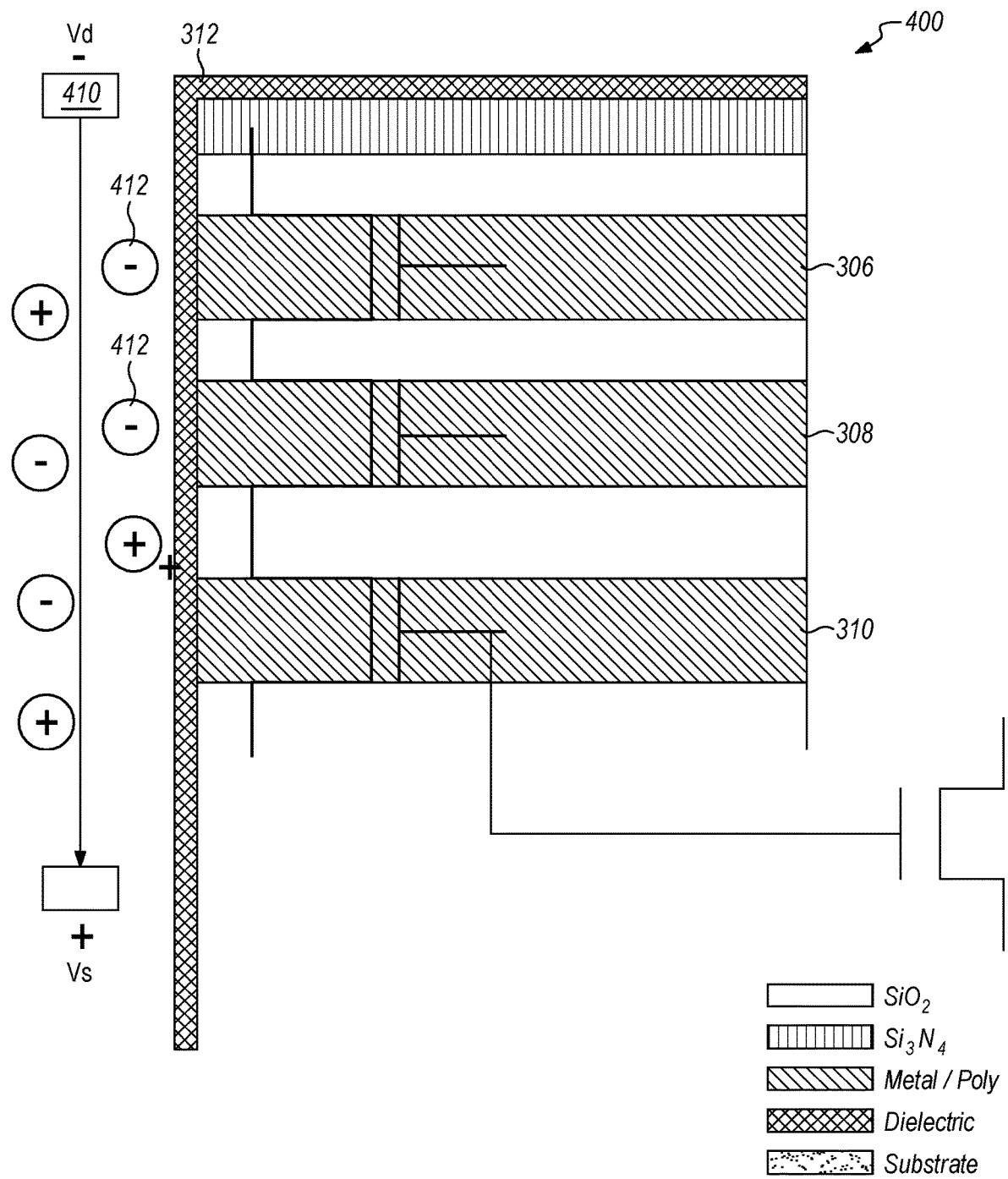

When a translocation rate control bias signal 410 for column and row voltages (e.g., Vd) is applied to the 3D nanopore sensor array 400, row and column inhibitory voltage/bias pulses are followed by a verify (sensing) voltage/bias pulse (e.g., Vg1, Vg2), as described below. Vg3 and following electrodes (Vg4~VgN) are sensing and translocation electrodes. An exemplary signal 410 is depicted in FIG. 4 overlaid on top of the 3D nanopore sensor array 400. Inhibitory biases are applied to deselect various column and row nanopore pillar channels/nanochannels, respectively. During sensing operation, both column and row (inhibitory) select nanoelectrodes are selected. The resulting surface charge 412 can be detected as a change in an electrical characteristic, such as current.

At the same time, the Vg3, Vg4 nanoelectrodes can detect current modulations resulting from passage of charged particles (e.g., DNA biomolecules) through or electrical attachment of charged particles (e.g., DNA biomolecules) to the interior surfaces/walls of the 3D vertical nanopore pillars/nanochannels. In some embodiments, the nanoelectrodes can detect current modulations using a variety of principles, including ion blockade, tunneling, capacitive sensing, piezoelectric, and microwave-sensing. It is also possible that ionic concentration or so called ionic current change in the electrode (detected by the reference electrode) can be amplified and accurately sensed by the attached CMOS transistor as shown in the FIG. 4.

Figure 5:
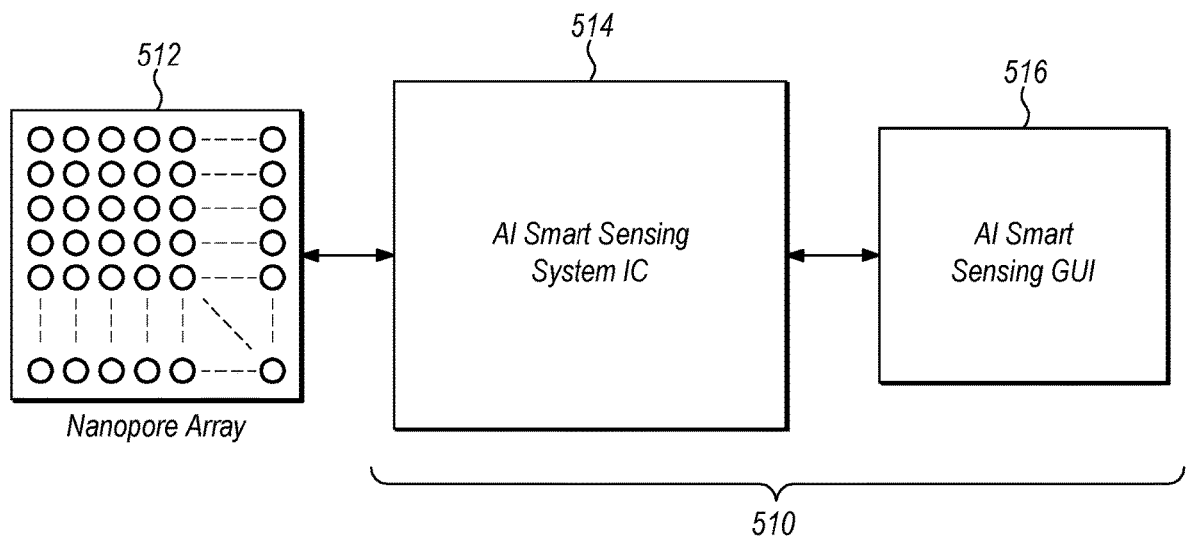
FIG. 5 schematically illustrates an Artificial Intelligence control and categorization system for use with a nanopore array according to some embodiments.

Exemplary Control and Categorization System for Use With Nanopore Based Gene Polymorphism Detection Device FIG. 5 depicts an Artificial Intelligence ("AI") control and categorization system 510 for use with a nanopore array (e.g., 3D) 512 according to some embodiments. The AI control and categorization system 510 includes an AI smart sensing system ("AISSS") 514, which may be embodied on an integrated circuit ("IC"), and an AI smart sensing graphical user interface ("GUI") 516. The AI control and categorization system 510 is configured to perform various tasks, including but not limited to control voltages applied to the nanopore array 512, calibrate the nanopore array 512, and analyze nucleic acid sequence data from the nanopore array 512 to identify a condition or disease associated with the nucleic acid sequence data from the nanopore array 512.

The nanopore array 512 includes M rows and N columns defining M×N nanopores formed from special multi-gate transistors as described above. The row and column selection voltage and biasing voltage for each nanopore for sensing DNA related charge information may be controlled by the AISSS 514. The AISSS 514 may receive, filter, and amplify a very small charge related signal (e.g., change in current) from the selected nanopore as a negatively charged DNA molecule passes therethrough. The AISSS 514 may also calibrate each nanopore channel of the nanopore array 512 before measuring the charge related signals and sending them for analysis.

A. AISSS Architecture

Figure 6:
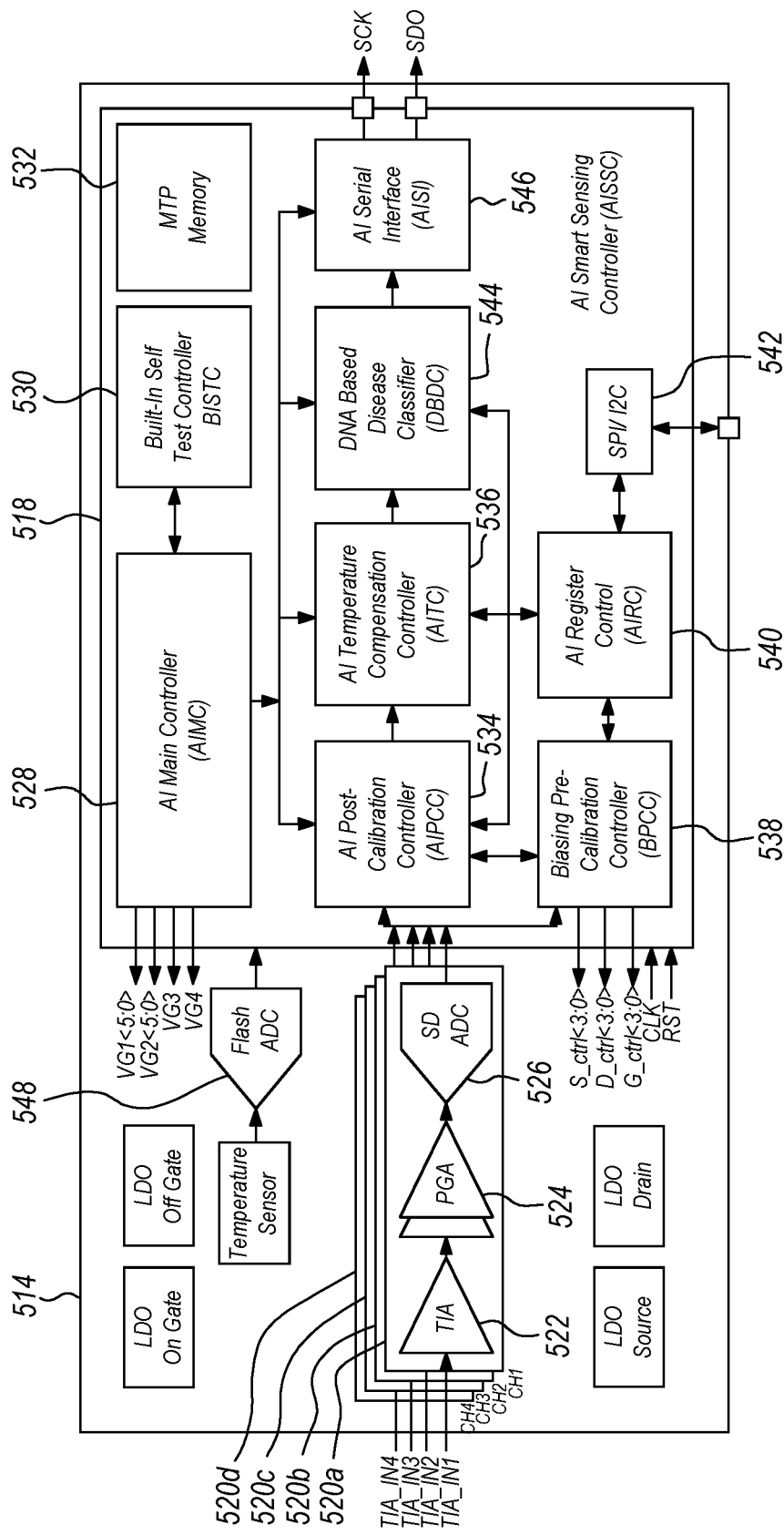
FIG. 6 schematically illustrates an Artificial Intelligence Smart Sensing System IC according to some embodiments.

FIG. 6 schematically depicts an AISSS IC 514 according to some embodiments. The architecture of the AISSS IC 514 is depicted in FIG. 6. The AISSS IC 514 includes an AI Smart Sensing Controller ("AISSC") 518 operatively coupled to four parallel analog front end ("AFE") channels 520a-520d. Each AFE 520a-520d includes a multi-stage transimpedance amplifier ("TIA") 522, a programmable gain amplifier ("PGA") 524, and a sigma-delta analog-to-digital converter ("SD ADC") 526. The AISSC IC 514 may process data from all four AFE channels 520a-520d in parallel. The AISSC 518 includes an AI Main Controller ("AIMC") 528, a Built-In Self Testing Controller ("BISTC") 530, an Multiple Time Programmable Memory ("MTP") 532, an AI Post Calibration Controller ("AIPCC") 534, an AI Temperature Compensation Controller ("AITC") 536, a Biasing Pre-Calibration Controller ("BPCC") 538, an AI Register Control ("AIRC") 540, a serial connector ("SPI/12C") 542, a DNA Based Disease Classifier ("DBDC") 544, an AI Serial Interface ("AISI") 546, and a flash analog-to-digital converter ("FLASH ADC") 548.

Each TIA 522 is configured to receive a very small charge related signal (e.g., in the nano-ampere ("nA") range) from a selected nanopore, and convert the signal to a voltage. Each PGA 524 amplifies the voltage from the corresponding TIA 522. Each SD ADC 526 converts the analog voltage signal generated by the PGA 524 into a digital signal for calibration and processing to extract characteristic/disease information. Due to non-linear characteristics of nanopores, before receiving the charge related signals/data from the nanopore array 512, each nanopore is calibrated to increase system accuracy.

B. System Calibration

Figure 7:
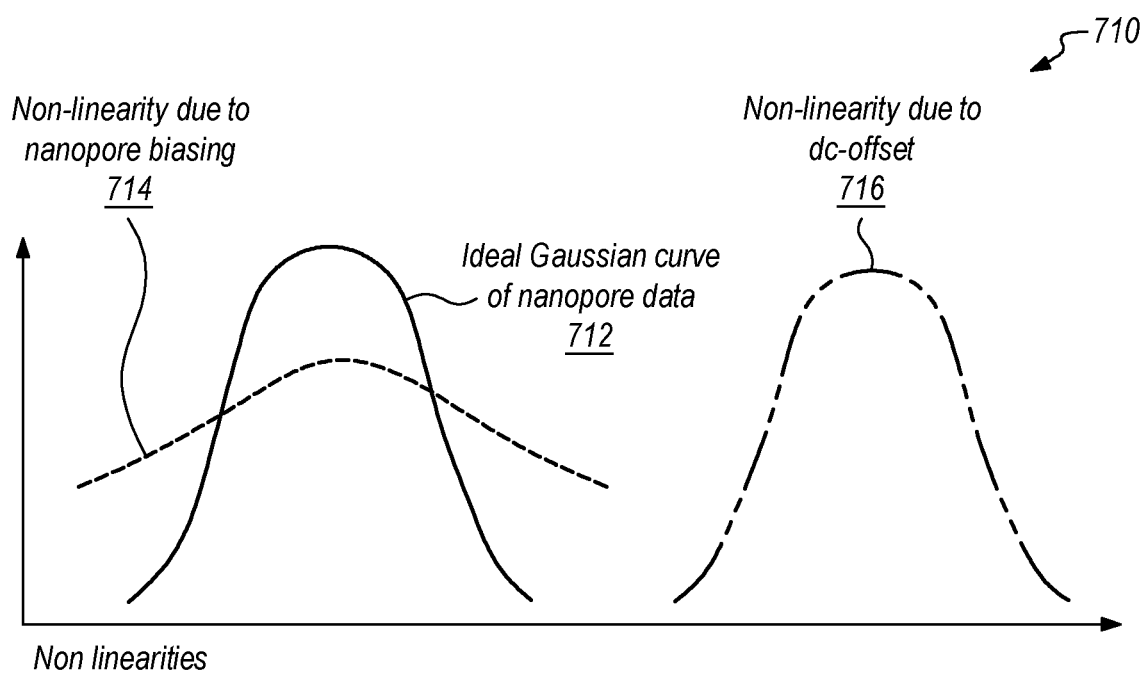
FIG. 7 is a graph depicting various Gaussian probability distribution curves of the charge related signals/data received from a nanopore array, according to some embodiments.

As described above, each nanopore of the nanopore array 512 is calibrated before collecting the charge related signals/data to improve system accuracy. FIG. 7 is a graph 710 depicting various Gaussian probability distribution curves of the charge related signals/data received by the AISSS 514 from the nanopore array 512 (see FIG. 5), according to some embodiments. Some of the curves are distorted from an ideal curve by the non-linear characteristics of the nanopores. These effects may be corrected by the AISSS 514 during one or more calibration steps.

The curves may be Gaussian plots of the number of samples at each charge related signals/data value from the nanopores of the nanopore array 512. Multiple samples are collected from each nanopore. Then the data for all nanopores is plotted as a Gaussian curve for data analysis. In a Gaussian curve, the mean is the center of Gaussian distribution, which is highest point on the curve. The relative frequency of any particular charge related signal/data value is highest near the mean indicating the most of nanopore samples are close to the mean. The relative frequency drops as the charge related signal/data values on the curve moves away from the mean. The X-axis tracks the charge related signal/data values and the Y-axis tracks the number of (e.g., randomly selected) nanopore samples having each value. Therefore, the Gaussian curves depict normalized distributions (i.e., relative frequency of each sample charge related signal/data) of data from the nanopores.

Curve 712 depicts an ideal Gaussian curve of data from all nanopores of a nanopore array 512. This curve 712 represents the most accurate distribution of data from the nanopore array 512. Curve 714 depicts a Gaussian curve of data from all nanopores of a nanopore array 512 that includes the effect of non-linear charge related signal/data response to nanopore biasing voltage. Curve 716 depicts a Gaussian curve of data from all nanopores of a nanopore array 512 that includes the effect of direct current ("DC") offset on the measured charge related signal/data.

Figure 8A:
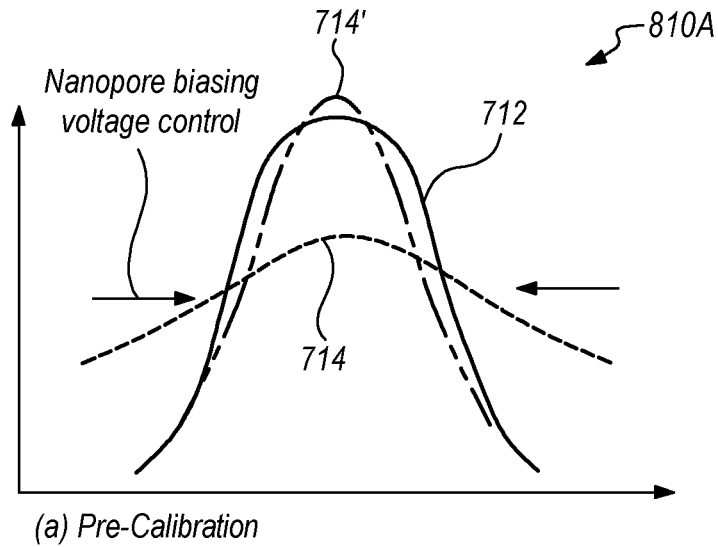
FIGS. 8A and 8B are graphs depicting various Gaussian probability distribution curves of the charge related signals/data respectively corresponding to pre- and post-calibration of charge related signals/data according to some embodiments.

In some embodiments, the AISSS 510 implements two different types of system calibration. In pre-calibration, the biasing voltage of each nanopore is adjusted by a pre-calibration algorithm to generate a signal curve that approximates the shape of the ideal Gaussian curve 712. Pre-calibration transforms curve 714 to a curve 714' that approximates the shape of ideal curve 712 (see graph 810A in FIG. 8A). During pre-calibration, the biasing voltage for each nanopore is swept from $V_{min}$ to $V_{max}$ (positive slope) or from $V_{max}$ to $V_{min}$ (negative slope) with a constant small step size and corresponding received signal/data (e.g., digital code) is compared with a reference value. The direction (slope) and magnitude (step-size) of the biasing voltage sweep may be configurable by the BPCC.

Figure 8B:
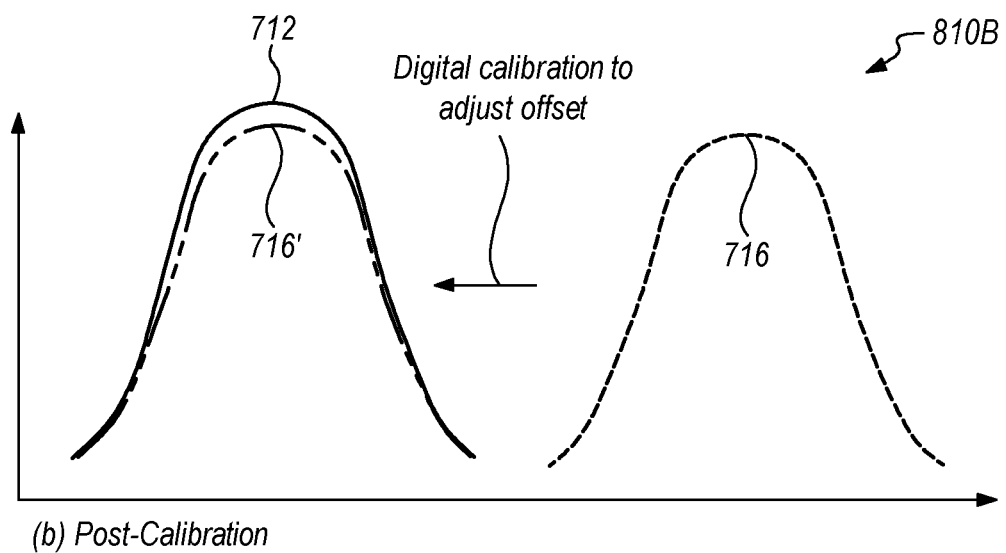

In post-calibration, the charge related signal/data of each nanopore is adjusted by a post-calibration algorithm to generate a signal curve that approximates the charge related signal/data of the ideal Gaussian curve 712. Post-calibration may be performed on the received signal/data (e.g., digital data). Post-calibration transforms curve 716 to a curve 716' that approximates the charge related signal/data of ideal curve 712 (see graph 810B in FIG. 8B). In post-calibration, the charge related signal/data of each nanopore is measured, compared to reference data to generate an offset value, and adjusted using the offset value to approximate the charge related signal/data values of the ideal Gaussian curve 712. The comparison and adjustment may be performed by the AIPCC.

Figure 9:
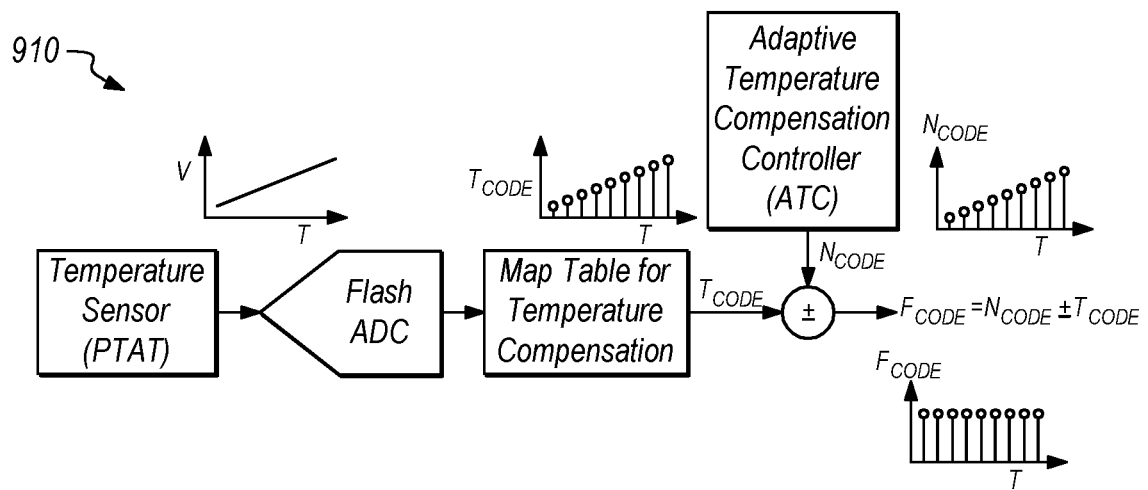
FIG. 9 schematically illustrates a temperature compensation process according to some embodiments.

Post-calibration also includes a temperature compensation process 910 as shown in FIG. 9. For any particular nanopore, its corresponding charge related signal/data values changes with temperature. This change is detected and subtracted/added to the charge related signal/data values to generate temperature independent charge related signal/data values that are consistent across a temperature range. FIG. 9 conceptually explains the temperature compensation process. The AISSS 504 may include or be operatively coupled to a temperature sensor ("PTAT"). The PTAT output voltage has a proportional relationship with the temperature of the nanopore array 512. The PTAT output voltage is converted to a digital code, $T_{CODE}$ by Flash ADC 548. A lookup table ("LUT")/map table is used to translate the temperature variation (i.e., $T_{CODE}$) to a value scaled to match the scale of the charge related signal/data. The scaled value is subtracted from/added to the AIPCC output charge related signal/data ("$N_{CODE}$") to generate the final temperature independent nanopore output charge related signal/data ("$F_{CODE}$").

Figure 10:
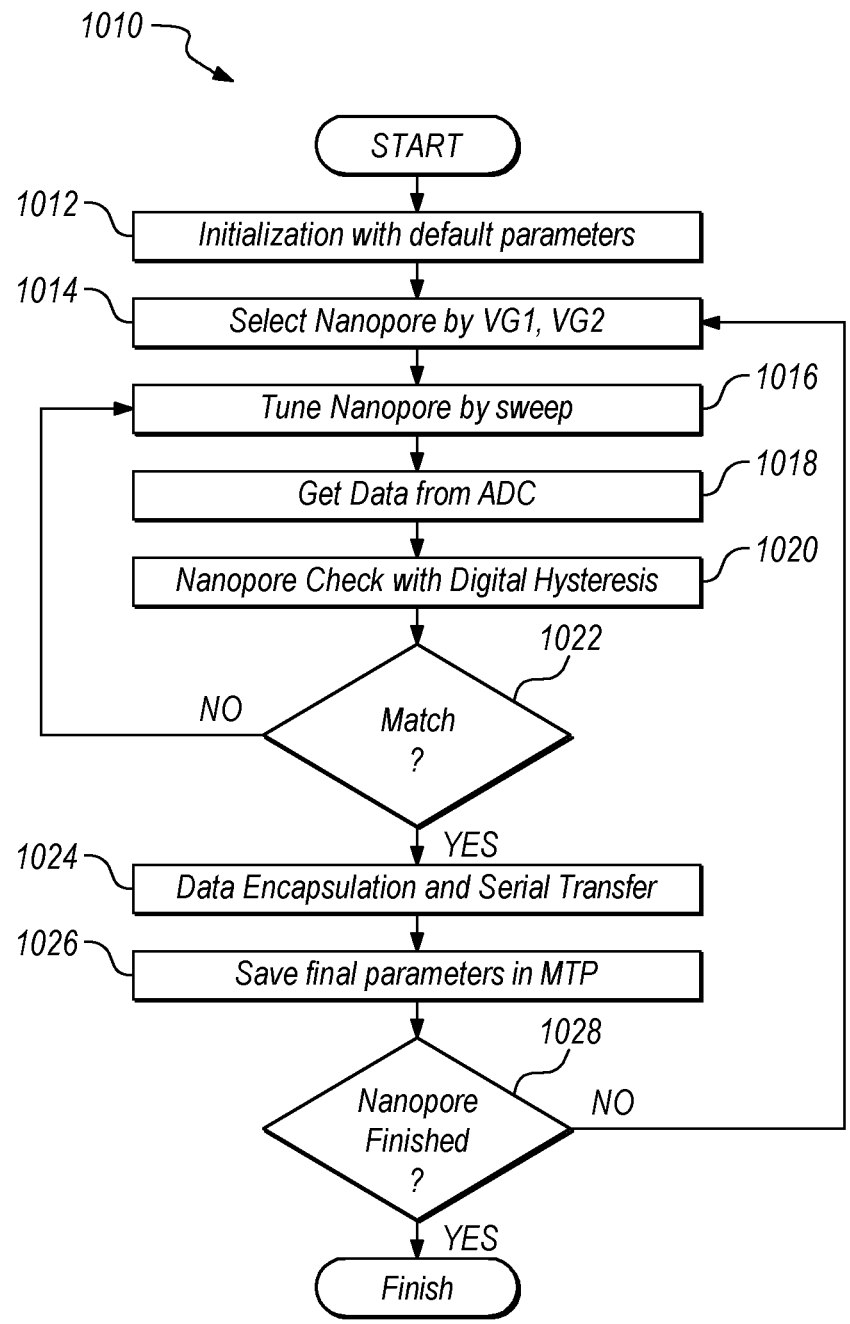
FIG. 10 is a flowchart depicting a pre-calibration method/algorithm according to some embodiments.

FIG. 10 is a flowchart depicting a pre-calibration method/algorithm 1010 according to some embodiments. At 1012, the AISSS 514 is initialized with default parameters. At 1014, a nanopore of the nanopore array 512 is selected by applying a VG1 and VG2. At 1016, the nanopore is tuned by sweeping a biasing voltage and receiving charge related signal/data as described above. At 1018, the AISSC 518 receives the charge related (digital) data from the ADC. At 1020, the received charge related signal/data is compared with reference data to check with Digital Hysteresis. If the received charge related signal/data is nota match (within certain thresholds) with the reference data 1022, the method/algorithm 1010 returns to 1016 to retune the selected nanopore. If the received charge related signal/data is a match (within certain thresholds) with the reference data 1022, the parameters are encapsulated (e.g., associated with the VG1 and VG2 and hence the selected nanopore) and transferred (via SPI/12C) at 1024, then stored in the MTP Memory at 1026. At 1028, it is determined whether all of the nanopores in the nanopore array 512 have been pre-calibrated. If they have not, the method/algorithm 1010 returned to 1014 to select the next nanopore to be pre-calibrated. If they have, the method/algorithm 1010 is completed.

Figure 11:
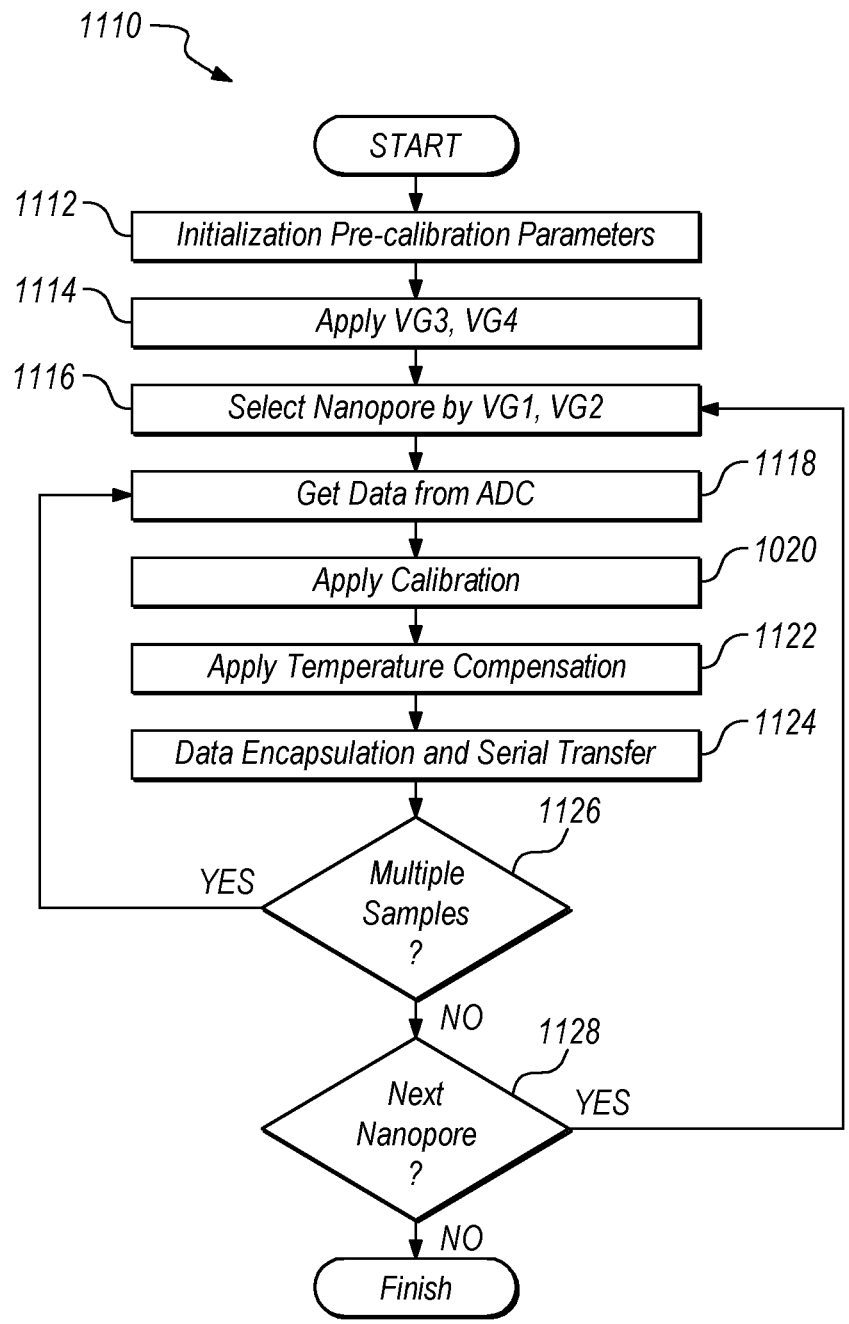
FIG. 11 is a flowchart depicting a post-calibration method/algorithm according to some embodiments.

FIG. 11 is a flowchart depicting a post-calibration method/algorithm 1110 according to some embodiments. At 1112, the AISSS 514 is initialized with default parameters. At 1114, biasing voltages VG3 and VG4 are applied to a nanopore of the nanopore array 512. At 1116, the nanopore is selected by applying a VG1 and VG2. At 1116, the AISSC 518 receives the charge related (digital) data from the ADC. At 1120, the offset value is applied to the received charge related signal/data. At 1122, the temperature compensation value is applied to the received charge related signal/data. At 1124, the modified charge related signal/data is encapsulated (e.g., associated with the VG1 and VG2 and hence the selected nanopore) and transferred (via SPI/12C for storage, classification, etc.) at 1124. At 1126, it is determined whether another sample has been collected at the nanopore. If another sample has been collected, the method/algorithm 1110 returned to 1118 to post-calibrate the next sample. At 1128, it is determined whether all of the nanopores in the nanopore array 512 have been post-calibrated. If they have not, the method/algorithm 1110 returned to 1116 to select the next nanopore to be post-calibrated. If they have, the method/algorithm 1110 is completed.

C. Biopolymer Data Classification for Characteristic/Disease Detection

As described above, detection of biopolymer (e.g., gene) polymorphisms indicative of various conditions and diseases requires classification of large amounts of biopolymer related raw data (e.g., the pre- and post-calibrated charge related signals/data). The DBDC receives the pre- and post-calibrated charge related signals/data from the BPCC, the AIPCC, and the AITC. The DBDC then applies Deep Neural Network ("DNN") techniques to classify the DNA to detect various characteristics and/or diseases.

The DBDC may include Convolutional Neural Network ("CNN") having N layers with forward and backward propagation programmed in its chip module. The CNN may be configured to process the pre- and post-calibrated charge related signals/data to classify DNA to detect various characteristics and/or diseases. The detected characteristics and/or diseases (e.g., filter coefficients) may be stored in the MTP memory. The detected characteristics and/or diseases along with other pre- and post-calibrated charge related signals/data related information may be sent to a Graphical User Interface ("GUI") on a PC through the AISI module. The AISSC may also implement a parallel to serial converter with custom framing structure.

The AI Smart Sensing Controller (AISSC) performs pre-calibration, post calibration, and AI based DNA and characteristic/disease classification. As such, the nanopore array calibration and polymorphism classification systems described herein provide accurate, efficient, and rapid classification of biopolymer related raw data in the detection of polymorphisms and the corresponding conditions and diseases.

While systems and methods have been described herein relative to calibration and classification of DNA detection nanopore array systems, the calibration and classification systems and methods are not limited to DNA detection nanopore array systems.

The corresponding structures, materials, acts and equivalents of all means or step plus function elements in the claims below are intended to include any structures, materials, acts and equivalents for performing the function in combination with other claimed elements as specifically claimed. It is to be understood that while the invention has been described in conjunction with the above embodiments, the foregoing description and claims are not to limit the scope of the invention. Other aspects, advantages and modifications within the scope to the invention will be apparent to those skilled in the art to which the invention pertains.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. Other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A method of calibrating a nanofluidic device comprising a plurality of nanopore channels, a plurality of gating nanoelectrodes, and a plurality of sensing nanoelectrodes, the method comprising:
   a. applying a selecting voltage across a gating nanoelectrode of the plurality of gating nanoelectrodes to select a nanopore channel corresponding to the gating nanoelectrode;
   b. tuning the nanopore channel by
      applying a first biasing voltage across a sensing electrode of the plurality of sensing nanoelectrodes corresponding to the nanopore channel, and receiving a plurality of currents that are distributed over a plurality of probability frequencies from the sensing electrode in response to the applied first biasing voltage;

c. generating a calibration data set from the pluralities of frequencies and currents;

d. comparing the calibration data set with a reference data set, wherein the reference data set is a prior set of experimental data or a set of theoretically modelled data;

e. when the calibration data set differs from the reference data set by more than a predetermined threshold, repeating steps b to d with a second biasing voltage different from the first biasing voltage.

2. The method of claim 1, further comprising, f. when the calibration data set is within the predetermined threshold of the reference data set, storing respective values of the selecting voltage and a final biasing voltage, wherein when the final biasing voltage is applied to the sensing electrode, the calibration data set is within the predetermined threshold of the reference data set.

3. The method of claim 2, further comprising, when the calibration data set is within the predetermined threshold of the reference data set:

g. applying the selecting voltage and the final biasing voltage across the gating and sensing nanoelectrodes, respectively;

h. receiving a second plurality of currents that are distributed over a second plurality of probability frequencies from the sensing electrode in response to the applied final biasing voltage;

i. generating a detected data set from the second pluralities of frequencies and currents; and j. applying a temperature compensation to the detected data set to generate a final detected data set.

4. The method of claim 3, further comprising, when the calibration data set is within the predetermined threshold of the reference data set:

k. storing the respective values of the selecting voltage and the final biasing voltage, and the final detected data set.

5. The method of claim 4, further comprising repeating steps a to k with each of the plurality of nanopore channels.

6. The method of claim 4, wherein steps a to k are performed with digital current data.

7. The method of claim 4, further comprising;
adding an oligonucleotide to the nanofluidic device; and
analyzing the respective values of the selecting voltage and the final biasing voltage, and the final detected data set to identify an oligonucleotide.

8. The method of claim 7, wherein the oligonucleotide is associated with a genetic condition.

9. The method of claim 1, wherein the plurality of currents are received from an analog to digital converter.

10. The method of claim 9, wherein the analog to digital converter generates digital current data from analog current data.

11. The method of claim 10, wherein the digital current data corresponds to a plurality of nucleotides.

12. The method of claim 1, further comprising repeating steps a. to e. with each of the plurality of nanopore channels.

13. The method of claim 1, wherein the selecting voltage is applied across first and second gating nanoelectrodes.

14. The method of claim 1, wherein the first biasing voltage is applied across first and second translation nanoelectrodes.

15. The method of claim 1, wherein the reference data set corresponds to a Gaussian curve.

16. The method of claim 1, further comprising amplifying the plurality of currents.

* * * * *